(12) United States Patent
Palaskar

(10) Patent No.: US 10,327,879 B2
(45) Date of Patent: Jun. 25, 2019

(54) DEVICE FOR RECORDING CENTRIC JAW RELATION AND ORIENTATION JAW RELATION SIMULTANEOUSLY

(71) Applicant: Jayant Nandkumar Palaskar, Pune (IN)

(72) Inventor: Jayant Nandkumar Palaskar, Pune (IN)

( * ) Notice: Subject to any disclaimer, the term of this patent is extended or adjusted under 35 U.S.C. 154(b) by 82 days.

(21) Appl. No.: 15/319,709

(22) PCT Filed: Jul. 2, 2015

(86) PCT No.: PCT/IN2015/050058
§ 371 (c)(1),
(2) Date: Dec. 16, 2016

(87) PCT Pub. No.: WO2016/185483
PCT Pub. Date: Nov. 24, 2016

(65) Prior Publication Data
US 2017/0128180 A1 May 11, 2017

(30) Foreign Application Priority Data
May 15, 2015 (IN) .......................... 1912/MUM/2015

(51) Int. Cl.
*A61C 19/045* (2006.01)
*A61C 11/00* (2006.01)
*B23B 31/12* (2006.01)

(52) U.S. Cl.
CPC ............ *A61C 19/045* (2013.01); *A61C 11/00* (2013.01); *B23B 31/12* (2013.01)

(58) Field of Classification Search
CPC ....... A61C 19/04; A61C 19/045; A61C 19/05; A61C 11/00; A61B 5/1077; A61B 5/4542;
(Continued)

(56) References Cited

U.S. PATENT DOCUMENTS

| | | | | |
|---|---|---|---|---|
| 1,662,670 A | * | 3/1928 | Harter | A61B 5/107 33/514 |
| 1,976,045 A | * | 10/1934 | Sorenson | A61C 19/00 33/513 |

(Continued)

OTHER PUBLICATIONS

International Search Report and Written Opinion—PCT/IN2015/050058—ISA/IN—dated Mar. 14, 2016.

*Primary Examiner* — Wade Miles
*Assistant Examiner* — Shannel N Wright
(74) *Attorney, Agent, or Firm* — Seyfarth Shaw LLP

(57) ABSTRACT

The device for recording centric jaw relation and orientation jaw relation simultaneously is disclosed that provides an accurate and precise recording of centric jaw relation as well as orientation jaw relation recording and transfer. The device includes a central bar, a centric relation recorder, a dentulous adjustable fork or an edentulous fork, a semi-circular frame, a nasion pointer and an orbital pointer. The central bar is received by a plurality of clamping assemblies that adjustably position the nasion pointer, the adjustable fork or the edentulous fork and the centric relation recorder respectively. The device can be used in case of both, dentulous as well as edentulous subjects. The device can advantageously transfer the centric relation record to any semi-adjustable articulators or non-adjustable articulators.

4 Claims, 8 Drawing Sheets

(58) Field of Classification Search
CPC ..... A61B 5/4547; A61B 5/107; A61B 5/6814; B23B 31/12
USPC .............................................. 433/69, 72–75
See application file for complete search history.

(56) References Cited

U.S. PATENT DOCUMENTS

| | | | | |
|---|---|---|---|---|
| 2,107,534 A * | 2/1938 | Houser | .................. | A61B 5/107 33/513 |
| 2,574,427 A * | 11/1951 | Tully | .................... | A61C 19/045 33/513 |
| 3,200,497 A * | 8/1965 | Goodfriend | .......... | A61C 11/022 433/214 |
| 4,304,551 A | 12/1981 | Kawasaki | | |
| 4,330,277 A * | 5/1982 | Beu | ...................... | A61C 19/045 433/73 |
| 4,639,220 A * | 1/1987 | Nara | ..................... | A61C 19/045 433/68 |
| 4,695,252 A * | 9/1987 | Edwardson | .......... | A61C 19/045 433/73 |
| 4,892,480 A * | 1/1990 | Levandoski | .......... | A61C 19/045 433/73 |
| 5,188,529 A | 2/1993 | Luth | | |
| 6,109,917 A * | 8/2000 | Lee | ...................... | A61C 19/045 433/68 |
| 7,048,539 B2 * | 5/2006 | Mack | ................... | A61C 19/045 433/73 |
| 2007/0178425 A1* | 8/2007 | Driscoll | ................ | A61C 19/04 433/73 |
| 2010/0143859 A1* | 6/2010 | Lang | .................... | A61C 19/045 433/73 |
| 2012/0244487 A1* | 9/2012 | Tamburrino | .......... | A61C 19/045 433/7 |
| 2013/0084537 A1* | 4/2013 | Cho | ..................... | A61C 19/045 433/29 |

* cited by examiner

DEVICE FOR RECORDING CENTRIC JAW RELATION AND ORIENTATION JAW RELATION SIMULTANEOUSLY

FIELD OF THE INVENTION

The invention relates to a device for recording centric jaw relation and orientation jaw relation simultaneously and particularly to a device for an accurate and precise recording of centric jaw relation as well as orientation jaw relation recording and transfer and more particularly to a device for dentulous as well as edentulous subjects that advantageously guides the mandible such that, its condyle head achieves the most superior and anterior position as per the latest definition given in Glossary of Prosthodontics Terms (GPT)-8.

BACKGROUND OF THE INVENTION

Centric jaw relation (CR) is a complex and controversial concept in dentistry. Main reason for the controversies is because its definition changed many times during last ten decades. Position of the head of the condyle during centric jaw relation position is the reason for most of the controversies. With the advancements in the field of oral radiology now it is understood that the head of the condyle does not attain most retruded unstrained position but it attains most anterior and superior position in the glenoid fossa. Centric jaw relation remains complex because the latest Glossary of Prosthodontic Terms (GPT)-8 continues to give seven definitions for centric jaw relation and some of the definitions are contradictory to each other. Another reason is as per latest GPT-8 the centric jaw relation definition, which is widely accepted, relates CR to so many clinically invisible parts making it difficult for the operator to follow its description in clinical dentistry. There is no device which will help the operator to guide the head of the condyle to attain this position as per the description given in the definition. Recording CR is very important step because it is the only relationship of the mandible to the maxilla which is repeatable, reproducible and recordable.

CR is defined as per the latest GPT-8 and widely accepted, "the maxillo-mandibular relationship in which the condyles articulate with the thinnest avascular portion of their respective discs with the complex in the anterior-superior position against the slopes of the articular eminences. This position is independent of tooth contact. This position is clinically discernible when the mandible is directed superiorly and anteriorly. It is restricted to a purely rotary movement about the transverse horizontal axis".

Apart from recording centric jaw relation other important relationship of the jaws with the Temperomandibular joint (TMJ) which is known as orientation jaw relation which is to be recorded using a facebow. Maxilla is a part of the cranium and is a fixed entity when the teeth of both jaws come in contact; mandible gets related to the maxilla so that the entire craniomaxillary complex is articulated with a moving bone, which is the mandible. The maxilla is oriented uniquely to the TMJ/cranium and this positioning differs from individual to individual. The anatomy of maxilla and the temporomandibular joint varies from person to person. Recording of the opening axis of the patient and its transfer to the articulator is very important for the occlusion developed on the articulator to remain same when the prosthesis is transferred to the patient's mouth, is the logic behind recording orientation jaw relation.

Centric jaw relation is an old concept in dentistry. There are over 26 different definitions of centric jaw relation since 1926. It is a position which is the only position of the mandible that is repeatable, recordable and reproducible. According to old definition of the centric jaw relation, the location of both condyles was considered to be attaining the most retruded position, however now it is understood that it attains most anterior and superior position in the glenoid fossae. The accuracy of recording is highly dependent on the individual understanding of the concept, skills, judgement, method chosen by individual dentist, their experience, etc. Centric jaw relation is the mandibular jaw position in which the head of the condyle is situated as far anterior and superior as it possibly can within the glenoid fossa.

Dentists use various conventional methods and devices to obtain precise location and recording of centric jaw relation which includes physiological methods like tactile or interocclusal check record method, pressure less method, pressure method or functional methods like needlehouse method, patterson method or graphic methods like intraoral method, extraoral method, and radiographic method. In order to record the centric jaw relation, it is important that both condyles be seated in their most superior and anterior position in the glenoid fossae. However, there exists no single device or instrument to achieve a precise location and recording of a centric jaw relation in edentulous and dentulous patients that can be accepted universally. There does exist a precise single method i.e. graphic recording which is most commonly used in edentulous patients with good alveolar ridges, however it has its own limitation and cannot be used for all the patients.

Similarly, the face bow transfer which establishes the relationship between the maxilla and the TMJ. i.e the relationship of the maxilla to the opening axis so that the maxillary cast can be mounted on the articulator in the correct anatomical position is another important aspect in dentistry and face bow is a device that is used to record the relationship of the jaws to the temporomandibular joints or the opening axis of the jaws and to orient the cast in the same relationship to the opening axis of the articulator. There are many existing face bow recording devices for achieving the required face bow transfer. However, there is no single device in prior art that allows a combination of centric jaw relation recording and face bow recording and its transfer in one sitting of the patient.

U.S. Pat. No. 3,643,332A discloses a method for measuring the movements of the lower jaw (mandible) relative to the upper jaw by selecting two points at a fixed distance apart on the horizontal axis of rotation of the subject's mandible, one on each side of subject's head and at substantially equal distances from the subject's head. This prior art document allows only face bow transfer and does not record centric jaw relation.

Another patent document EP950384B1 discloses an apparatus for tracing to record a centric jaw relation of a patient, particularly by a tracing apparatus in which a stylus is used to record a centric jaw relation of a patient for the fabrication of a prosthesis or dentures is coupled to a nut-shaped ball supported by a base plate mounted to a dentition and a support plate threadedly coupled to the base plate in such a fashion that it can be selectively pivotable, thereby eliminating use of any separate dentition supporting wires. However, the disclosed apparatus may cause injury to the patient due to the presence of the stylus and there could also be chances of uneven positioning of the apparatus that would ultimately give inaccurate recordings.

Another prior art document U.S. Pat. No. 3,750,289A discloses the centric jaw relation device that comprises of an upper frame and a lower frame which are hinged together along the condylar axis by a joint which permits relative movement only by rotation in a medial plane. However, this prior art references can only be used in case of edentulous patients and can only have its application in face bow transfer and not for centric jaw relation recording per se. Further, the devices of the prior art have a complex structure, and may cause injury to the patient. These devices though may provide satisfactory jaw relation recordings and face bow transfer, but require multiple sittings and appointments of the patients for face bow transfer and centric recording procedure. There is no device in art that provides both the procedures in one appointment. Further, most of the prior art devices for recording of centric jaw relation can only be used in case of edentulous patients. It is found that there has not been a single attempt to develop a device for recording centric jaw relation as per the latest definition as per GPT-8.

Thus, to achieve an accurate and precise centric jaw relation recording as well as face bow recording and transfer or orientation jaw relation simultaneously of subjects is an essential criterion for restoration of function, facial appearance, and maintenance of subject's oral health. Inaccurate centric jaw relationship will eventually lead to failure of a prosthesis leading to re-fabrication, which is a time consuming and a costly affair. Therefore, there exist a need for a centric jaw relation recording device that gives accurate recording of centric jaw relation and which allows orientation jaw relation as well, thereby avoiding multiple appointments for the subjects and a device that is safe and that can be used in both, dentulous as well as edentulous subjects.

SUMMARY

The present invention discloses a device for recording centric jaw relation and orientation jaw relation simultaneously of a dentulous subject in a single step. The device comprises a centric relation recorder that includes a calibrated rod, a calibrated slider and an arcuate grip. The calibrated rod includes a predefined first main scale and the calibrated slider includes a predefined second scale that records a centric jaw relation of a subject through the arcuate grip thereby adjusting the calibrated rod and calibrated slider. The calibrated slider is freely movable within the calibrated rod along a predefined axis thereof. A dentulous adjustable fork has a first curved end and a second straight end, wherein the first curved end has a pair of arms attached at a predefined position to facilitate fastening of a desired recording material and the second straight end is attached to the central rod. A first combination of reference points includes a semi-circular frame and a nasion pointer, wherein the semi-circular frame has two posterior points of reference and the nasion pointer defines a first anterior point of reference. A second combination of reference points includes a semi-circular frame and an orbital pointer, wherein the semi-circular frame has two posterior points of reference and the orbital pointer defines a second anterior point of reference. The nasion pointer and the orbital pointer alternately define a third point of reference. The third point of reference varies as per semi-adjustable articulator.

The centric relation recorder is a first recorder that records an accurate and precise centric relation of jaw. The semi-circular frame with the two combinations of reference points is a second recorder that records orientation jaw relation of the dentulous subject. The centric relation recorder, the nasion pointer and the adjustable fork are positioned on a predefined clamping assembly having a plurality of screws, a plurality of locks and a connector. The centric relation recorder, the nasion pointer and the adjustable fork are perpendicular to the central bar. The centric relation recorder, the nasion pointer and the adjustable fork adjustably position at a predefined position on the central bar thereby adjusting respective screws in horizontal, vertical, forward and backward movements thereof. The orbital pointer positions at a predefined location on the semi-circular frame such that the semi-circular frame is parallel to the inter-pupillary line. The device guides the mandible in such a way that the head of the condyle in the glenoid fossa, along with its respective complexes attain most anterior and superior position on either side, thereby resulting into an accurate and precise centric jaw relation recording. The calibrated slider is fine tuned until firm resistance is felt by an operator of said device.

A device for recording centric jaw relation and orientation jaw relation simultaneously of an edentulous subject in a single step comprises a centric relation recorder that includes a calibrated rod, a calibrated slider and an arcuate grip. The calibrated rod includes a predefined first main scale and a calibrated slider includes a predefined second scale that records a centric jaw relation of a subject through the arcuate grip thereby adjusting the calibrated rod and calibrated slider. The calibrated slider is freely movable within the calibrated rod along a predefined axis thereof. An edentulous fork has a first curved end and a second straight end, wherein the first curved end has a C-clip attached at a predefined position to facilitate fastening to maxillary and mandibular wax rims and the second straight end is attached to the central rod. A first combination of reference points includes a semi-circular frame and a nasion pointer, wherein the semi-circular frame has at least two posterior points of reference and the nasion pointer defines a first anterior point of reference. A second combination of reference points includes a semi-circular frame and an orbital pointer, wherein the semi-circular frame has two posterior points of reference and the orbital pointer defines a second anterior point of reference. The nasion pointer and the orbital pointer alternately define a third point of reference. The third point of reference varies per semi-adjustable articulator.

The centric relation recorder is a first recorder that records an accurate and precise centric jaw relation of jaw. The semi-circular frame with the two combinations of reference points is a second recorder that records orientation jaw relation of the edentulous subject. The centric relation recorder, the nasion pointer and the edentulous fork are positioned on a predefined clamping assembly having a plurality of screws, a plurality of locks and a connector. The centric relation recorder, the nasion pointer and the edentulous fork are perpendicular to the central bar. The centric relation recorder, the nasion pointer and the edentulous fork are adjustably positioned at a predefined position on the central bar thereby adjusting respective screws in horizontal, vertical, and forward and backward movements thereof. The orbital pointer positions at a predefined location on the semi-circular frame such that the semi-circular frame is parallel to the inter-pupillary line. The device guides the mandible in such a way that the head of the condyle in the glenoid fossa, along with its respective complexes attain most anterior and superior position on either side as defined in GPT-8, thereby resulting into an accurate and precise centric jaw relation recording. The calibrated slider is fine tuned until firm resistance is felt by an operator of said device.

A method for recording centric jaw relation and orientation jaw relation simultaneously of a dentulous subject in a single step comprises the steps of; making an occlusal jig in an acrylic resin or any other suitable material thereby subjecting mandibular anterior teeth of the subject in such a way that it disoccludes maxillary and mandibular teeth during all possible movements thereon. An adjustable fork is adjusted in between maxillary and mandibular teeth of the subject in such a way that it does not come in between maxillary and mandibular teeth and a double layer of a preferred perforable recording material is wrapped onto the adjustable fork to support the recording material from sides. A semi-circular frame is oriented and stabilized along an anterior side of the subject's face thereby approximating an orbital pointer at a predefined level of subject's infraorbital notch or alternatively nasion pointer at a predefined position over nasion depending on the semi-adjustable articulator being used. A centric relation recorder is fixed over the subject's chin by adjusting a predefined calibrated rod and a predefined calibrated slider. The readings on the calibrated rod and calibrated slider are noted and the above the step is followed at least three times thereby keeping the occlusal jig in the predefined position. The adjustable fork and the centric relation recorder are positioned back to the noted reading of above said step and the subject is asked to bite the recording material in one go. The nasion pointer, adjustable fork and centric relation recorder are tightened by respective screws for ensuring that the orbital pointer corresponds to the infra orbital notch or alternatively the nasion pointer corresponds to the nasion to be used as the third point of reference. All the respective screws of the centric relation recorder and nasion pointer are loosened to remove the semi-circular frame of the subject's face along with the adjustable fork for and the recorded indentations are noted on to the recording material. Said recorded indentations are transferred to the semi adjustable articulator such that indirect transferring of the recorded indentations or inter occlusal record is achieved by transferring inter occlusal record to the semi adjustable articulator. The transfer is done using a transfer jig of the articulator or said record is transferred to the semi-adjustable articulator by a direct transfer.

A method for recording centric jaw relation and orientation jaw relation simultaneously of an edentulous subject comprises the steps of: correct vertical jaw relation is recorded and it is ensured that there is no gap between maxillary and mandibular wax rims at occlusal vertical dimensions thereof. A semi-circular frame is oriented and stabilized along an anterior side of the subject's face thereby approximating an orbital pointer in a predefined position at a predefined level of subject's infraorbital notch or alternatively nasion pointer in a predefined position over the nasion depending on the semi-adjustable articulator being used. A centric relation recorder is fixed over the subject's chin by adjusting a predefined calibrated rod and a predefined calibrated slider. The readings on the calibrated rod and calibrated slider are noted and said step is followed at least three times. Further, a fork for edentulous subjects is designed, wherein a pin is inserted in maxillary and mandibular wax rims anteriorly along a midline thereof. The centric relation recorder is placed back to the above noted reading and an edentulous fork is inserted in the midline in such a way that it seals maxillary and mandibular wax rims together. Both the rims are further sealed together additionally by stapler pins by placing it on either side buccally such that half of the pin is inserted into the maxillary wax rim and half of the pin is inserted into the mandibular wax rim. The nasion pointer, the edentulous fork and centric relation recorder are tightened by respective screws such that orbital pointer corresponds to the infra orbital notch or alternatively the nasion pointer corresponds to the nasion thereby defining a third point of reference. Further, all respective screws of the centric relation recorder and the nasion pointer are loosened and the semi-circular frame is removed of the subject's face along with the edentulous fork having sealed maxillary and mandibular wax rims. The recorded sealed wax of the above step is transferred to the semi adjustable articulator either by direct transfer or indirect transfer. After transferring centric relation record and mounting of the casts to said articulator, the protrusive record is recorded for adjusting the condylar guidance on a semi-adjustable articulator.

The protrusive record is recorded, wherein the mandibular wax rim is reduced by 2-3 mm in height, except in second molar region on either side and in the central incisors region to maintain the vertical dimension. Inverted 'V' shaped notches are prepared on the maxillary wax rim in premolar and first molar region on either side. Further, 6 mm is subtracted from said recorded centric relation reading when a firm resistance was felt by the operator in order to obtain a protrusive reading of an edentulous subject. In a further step the centric recorder assembly is fixed at above said predefined protrusive reading and the recording material such as plaster of paris or any other suitable material is placed between the wax rims. The condylar guidance is adjusted according to said protrusive record and a lateral condylar guidance is adjusted by using Hanau's formula $L=H/8+12$. The device for recording centric relation and orientation jaw relation simultaneously of dentulous subject also records either centric relation or orientation jaw relation separately as per the requirement. The device for recording centric relation and orientation jaw relation simultaneously of edentulous subject also records either centric relation or orientation jaw relation separately as per the requirement. The centric relation record is transferred to any semi-adjustable articulators or non-adjustable articulators in case of the device for dentulous subjects as well as in case of device for edentulous subjects.

DETAILED DESCRIPTION OF THE DRAWINGS

Figure 1:
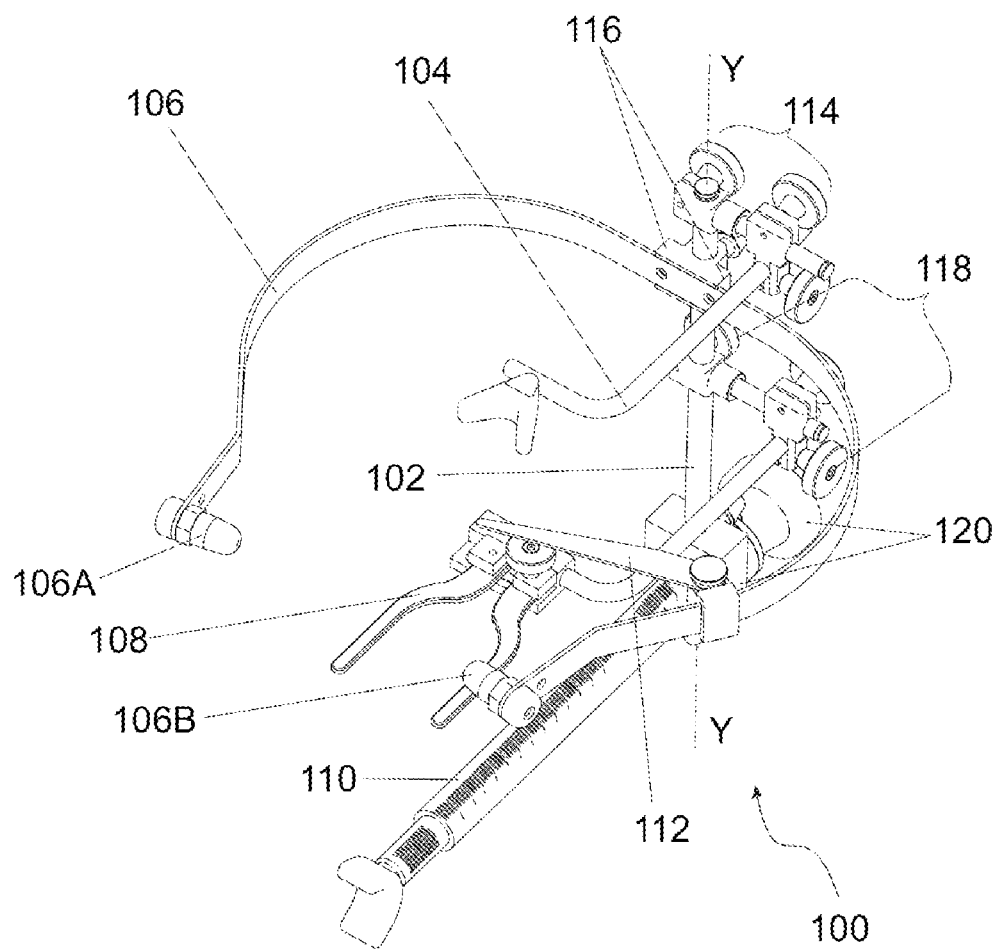
FIG. 1 is a front perspective view of a device for recording centric jaw relation and orientation jaw relation simultaneously of a dentulous subject in accordance with a preferred embodiment of the present invention.

Although specific terms are used in the following description for sake of clarity, these terms are intended to refer only to particular structure of the invention selected for illustration in the drawings, and are not intended to define or limit the scope of the invention.

Referring to FIG. 1, a device 100 for recording centric jaw relation and orientation jaw relation simultaneously of dentulous subjects in accordance with a preferred embodiment of the present invention is disclosed. The device 100 for recording centric jaw relation and orientation jaw relation simultaneously includes a central bar 102, nasion pointer 104, a semi-circular frame 106, an adjustable fork 108, a centric relation recorder 110 and an orbital pointer 112. The central bar 102 is receivable by a plurality of clamping assemblies 114,116, 118,120. The clamping assemblies 114, 118,120 adjustably position the nasion pointer 104, the adjustable fork 108, and the centric relation recorder 110 respectively. The central bar 102 is normal to the ground in a direction indicated by axis-Y. The nasion pointer 104 is adjustably positionable through a first clamping assembly 114. The semi-circular frame 106 is adjustably positionable on the central bar 102 through a second clamping assembly 116 such that the semi-circular frame 106 is positionable on the subject's face in accordance with the present invention. It is to be noted that the semi-circular frame 106 is made up of stainless steel that provides the property of spring action to the semi-circular frame 106, thereby making the frame 106 self centering. The second clamping assembly 116 attaches semi-circular frame 106 to the central bar 102. The adjustable fork 108 is adjustably positionable through a third clamping assembly 118 and the centric relation recorder 110 is adjustably positionable through a fourth clamping assembly 120. The first clamping assembly 114 clamps the nasion pointer 104 to the central bar 102, the second clamping assembly 116 clamps the semi-circular frame 106 to the central bar 102, the third clamping assembly 118 clamps the adjustable fork 108 and the fourth clamping assembly 120 clamps the centric relation recorder 110. The nasion pointer 104, the adjustable fork 108 and the centric relation recorder 110 are clamped such that the nasion pointer 104, the adjustable fork 108 and the centric relation recorder 110 are positioned perpendicular to the axis-Y of the central bar 102.

The semi-circular frame 106 is attached such that the central bar 102 is anterior to the semi-circular frame 106 and the semi-circular frame is positionable by the spring action of the semi-circular frame. The semi-circular frame 106 includes two extreme ends, a left end 106A and a right end 106B. The orbital pointer 112 is positionable at a predefined position on the semi-circular frame 106 in close proximity of the right end 106B. The nasion pointer 104, the adjustable fork 108, the centric relation recorder 110 are attached such that they are adjustably positionable horizontally along a predefined axis through the clamping assemblies 114,118, 120 respectively facing towards the two extreme ends 106A and 106B of the semi-circular frame 106 and are perpendicular to the Y-axis of the central bar 102. It is to be noted that the device 100 has two combinations of reference points, wherein the first combination includes the two extreme ends 106A and 106B of the semi-circular frame 106 acting as the two posterior points of reference and the nasion pointer 104 acting as a first anterior point of reference depending upon the type of articulator used. Similarly, the second combination is the two extreme ends 106A and 106B of the semi-circular frame 106 acting as the two posterior points of reference and the orbital pointer 112 acting as a second anterior point of reference depending upon the type of articulator used. The device 100 of the present invention includes a pair of recorder, wherein the fourth clamping assembly 120 having the centric relation recorder 110 acts as the first recorder for recording the centric relation and the semi-circular frame 106 along with either of the two combinations of reference points acts as a second recorder for recording of orientation jaw relation of the dentulous subject.

Figure 2:
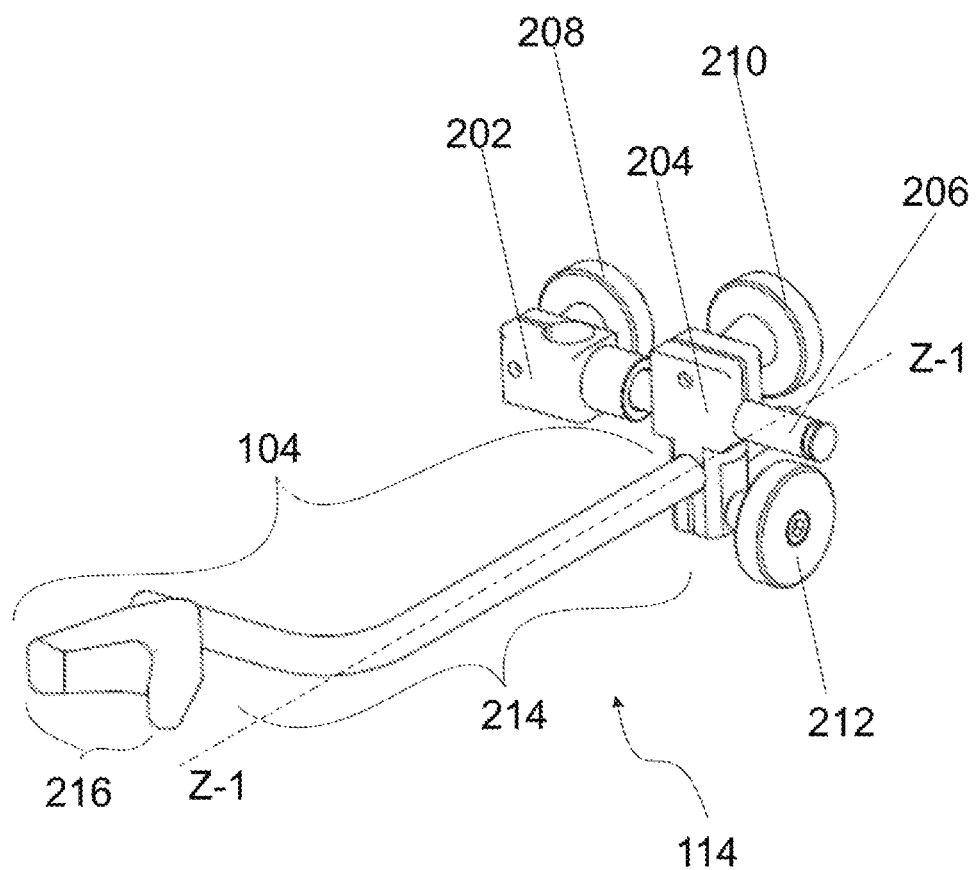
FIG. 2 is a front perspective view of a first clamping assembly of a device of FIG. 1.

Now referring to FIG. 2, a front perspective view of the first clamping assembly 114 of the device 100 for recording centric jaw relation and orientation jaw relation simultaneously for dentulous subjects is described. The first clamping assembly 114 includes a plurality of screws, a plurality of locks and a connector for adjustably clamping the nasion pointer 104 to the central bar 102. The first clamping assembly 114 includes a first lock 202, a second lock 204, a connector 206, a first screw 208, a second screw 210, a third screw 212 and the nasion pointer 104. The central bar 102 is adjustably couplable to the first lock 202 such that the central bar 102 is receivable within the lock 202 and is tightened by the first screw 208. The nasion pointer 104 includes an L-bar 214 and an arcuate pointer 216. The L-bar 214 has two ends. A first straight end of the bar 214 is adjustably couplable in the second lock 204 and a second curved end of the bar 214 is fixedly attachable to the arcuate pointer 216 at a predefined position. A first end of the connector 206 is horizontally couplable to the first lock 202 at a predefined position and a second end of the connector is receivable in the second lock 204 such that the connector 206 is perpendicular to the central bar 102 and is fixedly attached to the second lock 204 by tightening the second screw 210. The nasion pointer 104 is clamped such that the pointer 104 is perpendicular to the Y axis of the central bar 102. The nasion pointer 104 is adjustably moved in the forward and backward direction such that the arcuate pointer 216 is fixed to the subjects' nasion point that is over the nose bridge by adjusting the third screw 212. The nasion pointer 104 is horizontally adjustable along Z-1 axis at a predefined position either by loosening or tightening of the screw 210, vertically by adjusting screw 208, and forward or backward by screw 212 to achieve a required nasion pointer 104 length. The required length of the nasion pointer 104 is achieved by forward, backward, vertical and horizontal movement of the L-bar 214 by loosening of the respective screws and the nasion pointer 104 is locked at a predefined position as required by tightening of the respective screws. It is to be noted that the position of screws of the first clamping assembly may vary in other alternative embodiments of the device 100 for recording centric jaw relation and orientation jaw relation simultaneously.

Figure 3:
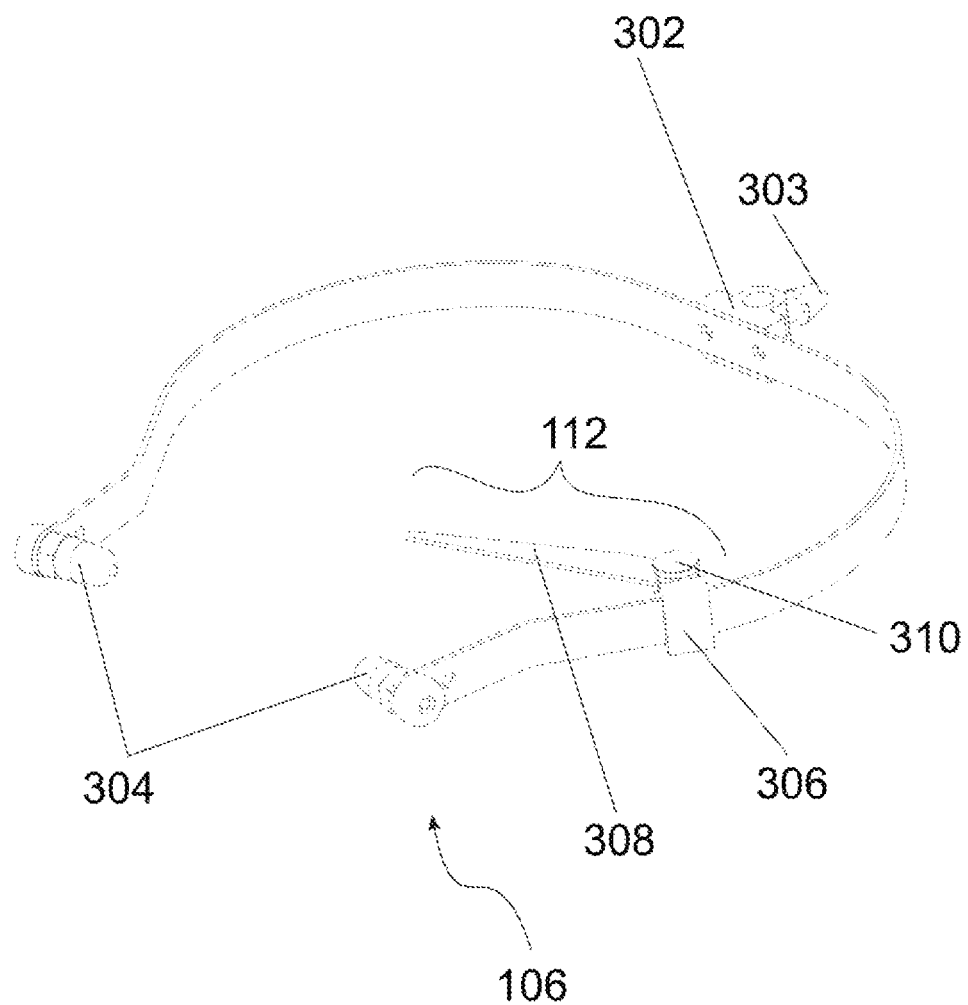
FIG. 3 is a perspective view of a semi-circular frame of a device of FIG. 1.

Referring to FIG. 3, a perspective view of the semi-circular frame 106 of the device 100 for recording centric jaw relation and orientation jaw relation simultaneously for dentulous subjects is described. The semi-circular frame 106 includes a centrally positioned bush 302, a screw 303, the orbital pointer 112, and a pair of ear plugs 304. The semi-circular frame 106 includes two extreme ends such that each of the ends includes the ear plugs 304. The orbital pointer 112 is positionable at a predefined position on the semi-circular frame 106 in close proximity of the right end. The semi-circular frame 106 is adjustably receivable by the second clamping assembly 116, such that the semi-circular frame 106 is removably positionable in the subject's ears through the spring action of the semi-circular frame and is connected to the central bar 102 through the clamping assembly 116, bush 302 and is lockable by the screw 303. The semi-circular frame 106 is removably attachable to the central bar 102 such that the central bar 102 is posterior to the semi-circular frame 106.

The orbital pointer 112 includes a socket 306, a pointer 308 and a bolt 310. The socket 306 includes a central notch. The orbital pointer 112 is positioned on the right side of the semi-circular frame at a predefined position such that the central notch of the socket 306 is fixed in the semi-circular frame 106 at a predefined position. The pointer 308 is fixedly positioned on a top end of the socket 306 via the bolt 310. The semi-circular frame 106 is oriented along the anterior side of the subject's face such that the pair of ear plug 304 is inserted into the subject's respective ears and semi-circular frame 106 is parallel to interpupillary line and the orbital pointer 112 is adjusted accordingly. The semi-circular frame 106 is stabilized over the subject's ears such that the orbital pointer 112 corresponds to the subject's infraorbital notch on the right side of the face as a third point of reference. The semi-circular frame 106 along with the two combinations of reference points is the second recorder for recording of orientation jaw relation of the dentulous subject. It is to be noted that the position of the orbital pointer 112 may vary in other alternative embodiments of the device 100 for recording centric jaw relation and orientation jaw relation simultaneously.

Figure 4A:
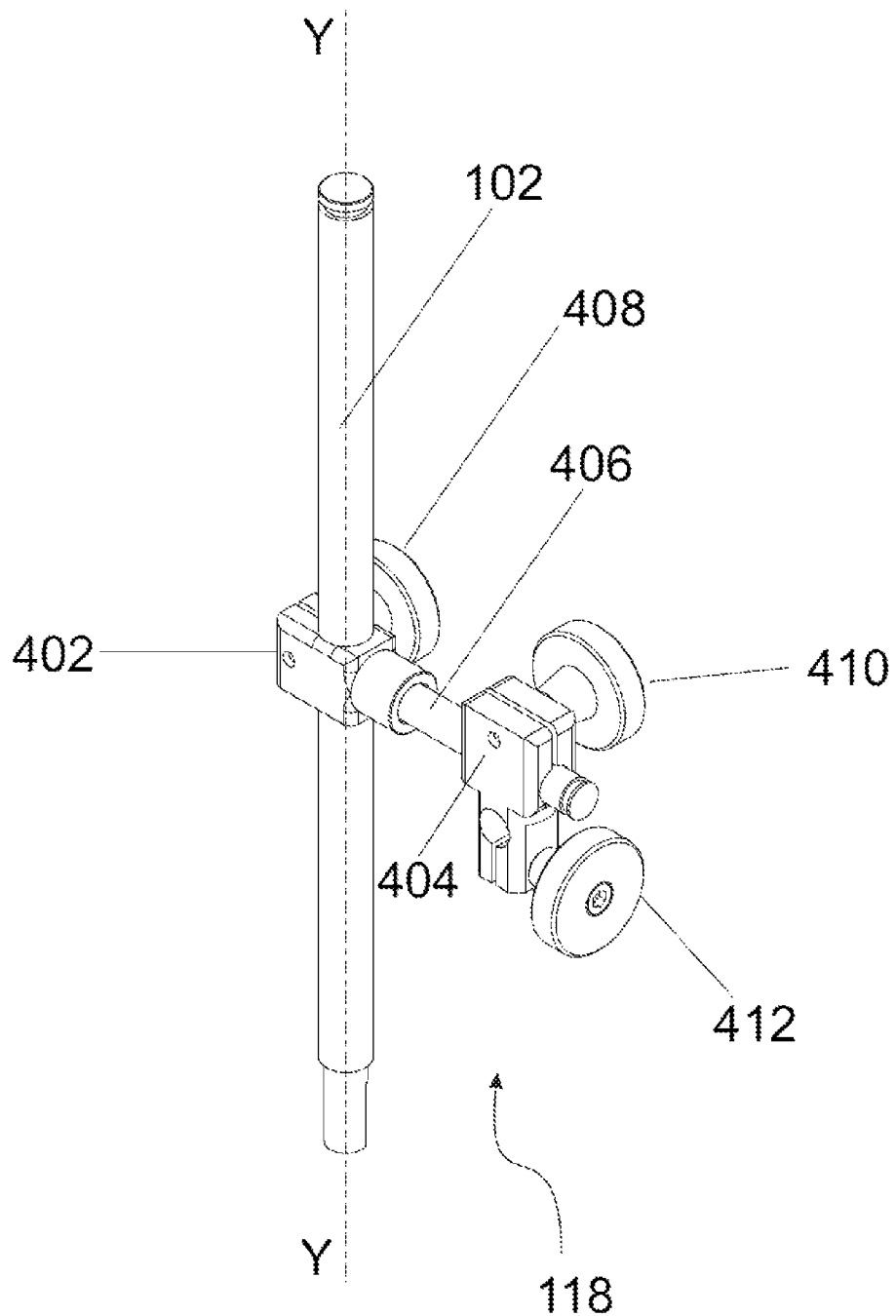
FIG. 4A is a perspective view of a third clamping assembly of a device of FIG. 1.
Figure 4B:
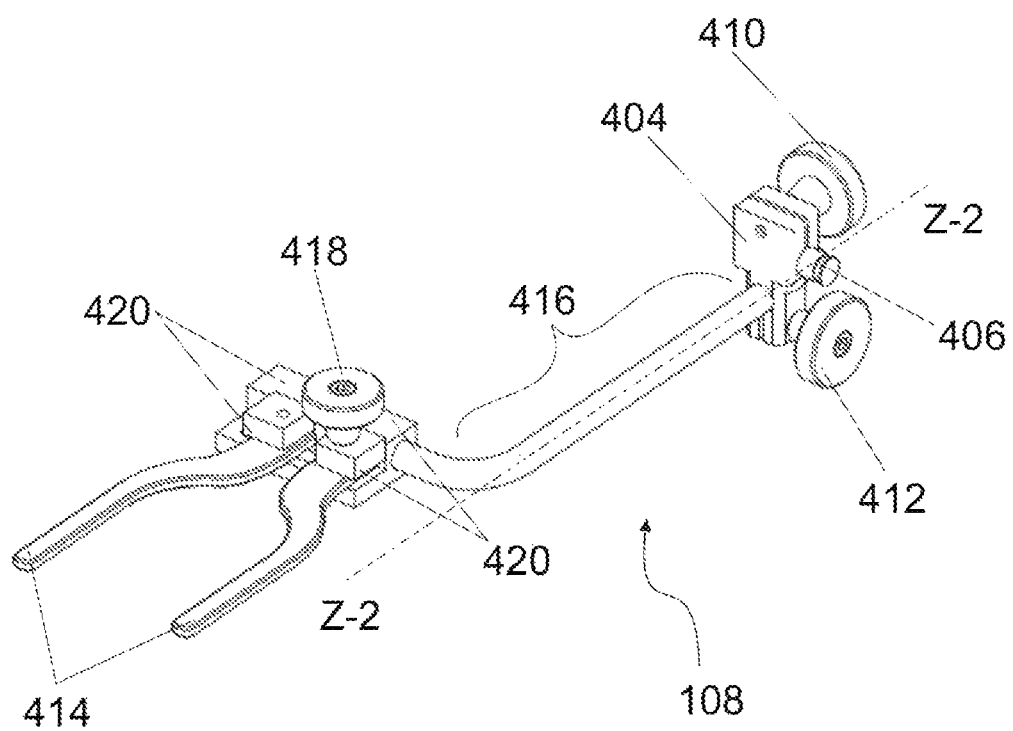
FIG. 4B is a perspective view of an adjustable fork of a device of FIG. 1.

Further, referring to FIGS. 4A and 4B, perspective view of a third clamping assembly 118 and an adjustable fork 108 of the device 100 for recording centric jaw relation and orientation jaw relation simultaneously for dentulous subjects is described. The third clamping assembly 118 includes a plurality of screws, a plurality of locks and a connector for adjustably clamping the adjustable fork 108 to the central bar 102. The third clamping assembly 118 includes a first lock 402, a second lock 404, a connector 406, a first screw 408, a second screw 410, a third screw 412 and the adjustable fork 108. The central bar 102 is adjustably couplable to the first lock 402 such that the central bar 102 is receivable within the lock 402 and is tightened by the first screw 408. The adjustable fork 108 includes two ends, a first curved end having a pair of arms 414 and a second straight end 416 adjustably couplable in the second lock 404. The first curved end of the fork 108 is adjustably attachable to the arms 414 at a predefined position. A first end of the connector 406 is horizontally couplable to the first lock 402 at a predefined position and a second end of the connector 406 is receivable in the second lock 404 such that the connector 406 is perpendicular to the central bar 102 and is fixedly attached to the second lock 404 by tightening the second screw 410. The adjustable fork 108 is clamped such that the adjustable fork 108 is perpendicular to the Y axis of the central bar 102. The adjustable fork 108 is horizontally adjustable along Z-2 axis at a predefined position either by loosening or tightening of the screw 410, vertically by 408 and forward or backward by 412 accordingly to achieve a required adjustable fork 108 length. It is to be noted that the position of screws of the third clamping assembly may vary in other alternative embodiments of the device 100 for recording centric jaw relation and orientation jaw relation simultaneously.

The arms 414 are adjustably couplable to the first curved end of the fork 108 and are fixedly adjustable by a screw 418 and a plurality of supports 420 such that the supports 420 clamp the arms 414 and connect the arms 414 to the fork 108, and the screw 418 adjustably tighten or loosen the arms 416 in a predetermined position. The pair of arms 414 of the adjustable fork 108 facilitates the fastening of a recording material. The recording material is a double layer of wax or any other suitable perforable material. The adjustable fork 108 is insertable into the subjects' mouth such that the pair of arms 414 does not interfere with the subjects' teeth while occluding.

The arms 414 are adjusted at a predefined position to achieve a required distance between the arms 414 without interfering the occlusion by adjusting screw 418. The arms 414 are lockable in a required positing by tightening screw 418. The required length of the adjustable fork 108 is achieved by forward, backward, vertical and horizontal movement of the straight end 416 by loosening of the respective screws and the adjustable fork 108 is locked at a predefined position as required by tightening of the respective screws. It is to be noted that the arms 414 of the adjustable fork 108 for dentulous subjects are customized according to the width of the subject's arch and is designed to record maxillary and mandibular occlusal record without any interference of the teeth.

Figure 5:
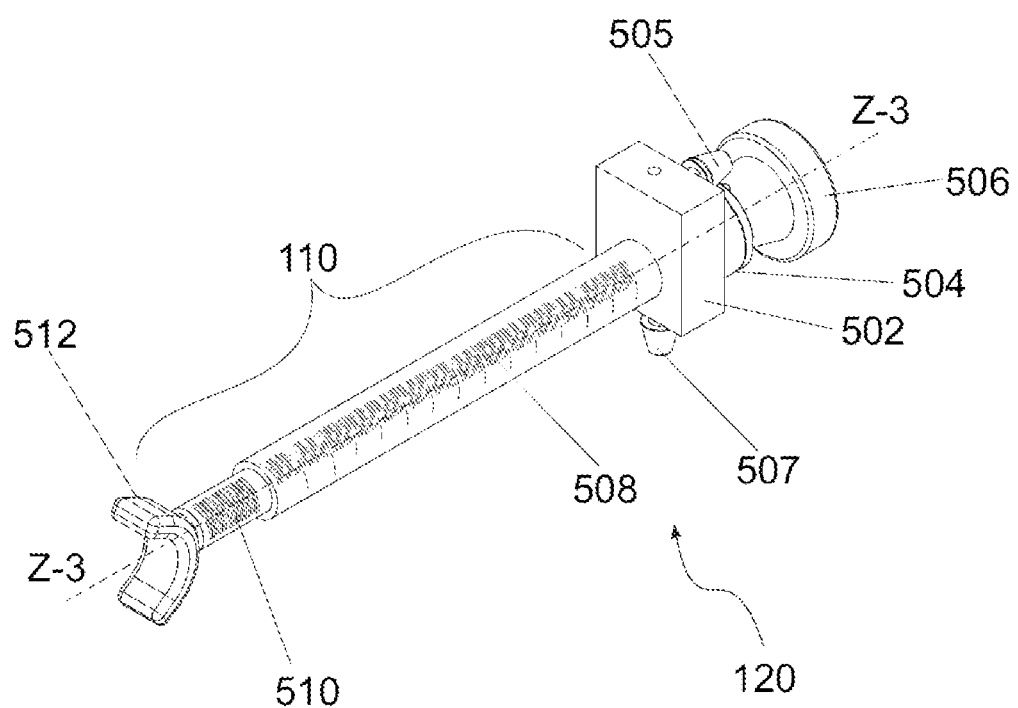
FIG. 5 is a perspective view of a fourth clamping assembly with a centric relation recorder of a device of FIG. 1.

Referring to FIG. 5, a perspective view of a fourth clamping assembly 120 and a centric relation recorder 110 of the device 100 for recording centric jaw relation and orientation jaw relation simultaneously for dentulous subjects is described. The fourth clamping assembly includes a bush 502, a collar 504, a plurality of screws 505, 506, 507 and the centric relation recorder 110. The centric relation recorder 110 includes a predefined calibrated rod 508, a predefined calibrated slider 510 and an arcuate grip 512. The centric relation recorder 110 is clampable to the fourth clamping assembly 120 such that the centric relation recorder 110 is adjustably positionable to the central bar 102 through the bush 502 that is connectable between the centric relation recorder 110 and the collar 504, and the bush 502 is tightened to the central bar 102 by the screw 505. The centric relation recorder 110 is perpendicular to the Y axis of the central bar 102. The rod 508 is movable along Z-3 axis and is adjustable at a predefined position by the screw 507. The centric relation recorder 110 is assembled such that the arcuate grip 512 is fixedly attached to the slider 510. The rod 508 receives the slider 510 such that the slider 510 is adjustable along the Z-3 axis by the screw 506 and is an integral part of the centric relation recorder 110.

The slider 510 has a diameter that is less than the rod 508 such that the slider 510 is adjustable into the rod 508 along the Z-3 axis and is freely movable inside the calibrated rod. The slider 510 is adjustable in the forward and backward direction at a predefined position either by loosening or tightening the screw 506 accordingly after positioning slider 510 accurately over the subject's chin. The slider 510 provides a linear motion to the arcuate grip 512. The rod 508 and the slider 510 of the centric relation recorder 110 are calibrated with a predefined scale for the recording of the centric jaw relation. The calibrated rod includes a predefined first main scale for recording of the centric jaw relation and the calibrated slider includes a predefined second scale for fine tuning and recording of the centric jaw relation of a subject by adjusting the rod at a predefined position by the arcuate grip and by fine adjustment done with the slider. It is to be noted that the required major adjustment is done by adjusting the rod 508, followed by fine adjustment by the slider 510 by moving the screw 506.

The arcuate grip 512 is positionable over the centre of the subject's chin such that the chin of the subject is in a relaxed position on the arcuate grip 512 of the centric relation recorder 110. The arcuate grip 512 of the centric relation recorder 110 is fixed over the centre of the subject's chin and the major required length of the recorder 110 is adjusted by adjusting 508 and tightening the screw 507 and further length can be achieved by tightening 506 until a strong resistance is felt by the operator.

In accordance to the present invention, subject's anterior occlusal jig is to be made by either acrylic resin or any other suitable material so that the subject's maxillary and mandibular teeth do not contact each other during any movement of the mandible i.e forward, backward and lateral etc. The centric relation recorder 110 is fixed over the subjects chin by adjusting the rod 508 as much as possible to a predefined length to ensure that the reading on the slider 510 is zero.

Figure 6A:
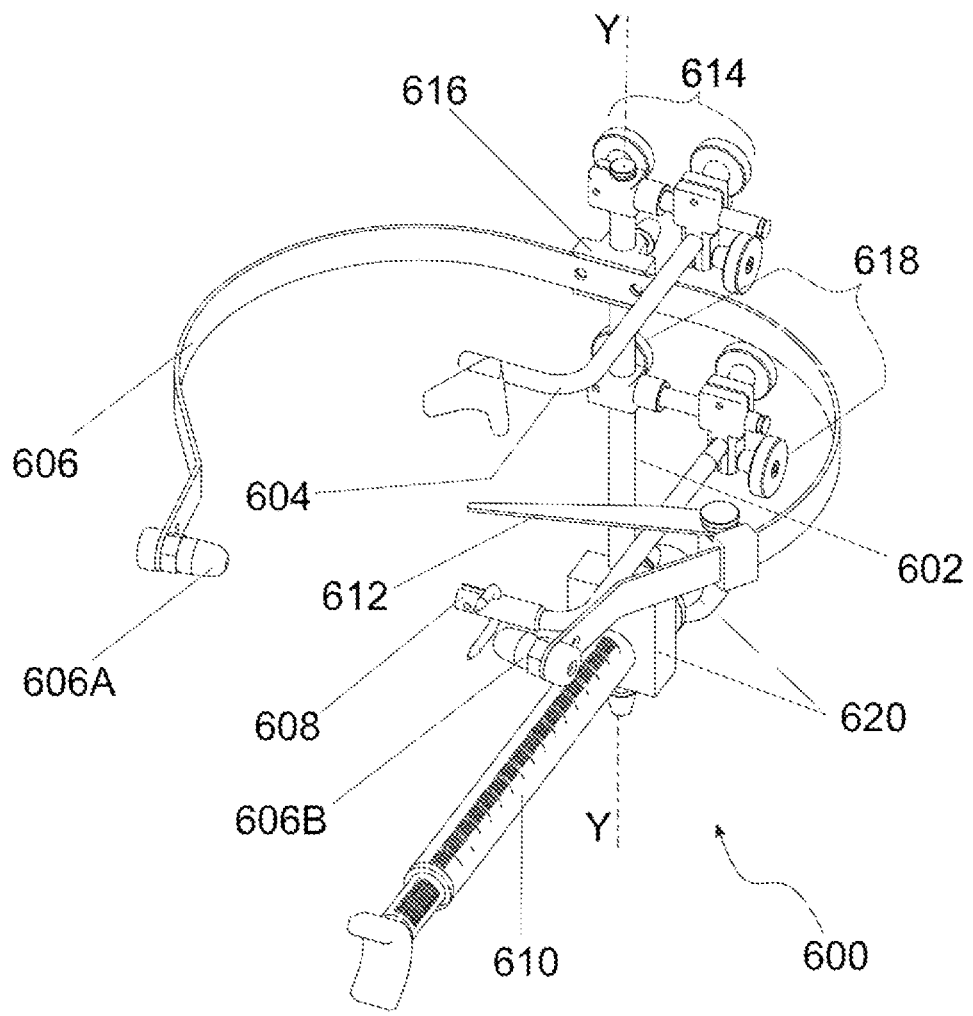
FIG. 6A is a front perspective view of a device for recording centric jaw relation and orientation jaw relation simultaneously of an edentulous subject in accordance with a preferred embodiment of the present invention.
Figure 6B:
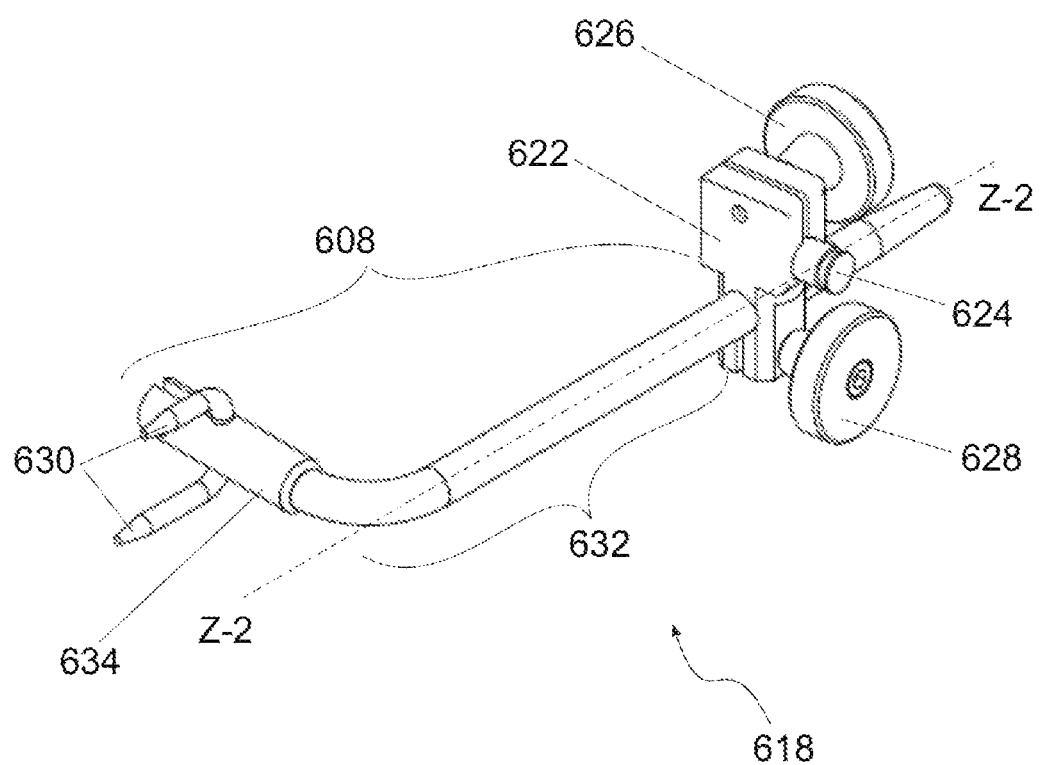
FIG. 6B is a front a perspective view of a third clamping assembly of a device of FIG. 6A.

In another embodiment, referring to FIG. 6A and FIG. 6B, a front perspective view of a device 600 for recording centric jaw relation and orientation jaw relation of edentulous subjects and a perspective view of third clamping assembly 618 of device 600 of the present invention is described. In this another embodiment, the device 600 of the present invention is used in edentulous subjects. The device 600 for recording centric jaw relation and orientation jaw relation simultaneously of edentulous subjects includes a central bar 602, nasion pointer 604, a semi-circular frame 606, an edentulous fork 608, a centric relation recorder 610 and an orbital pointer 612. The central bar 602 is positionable through a plurality of clamping assemblies 614,616, 618, 620. The clamping assemblies 614, 618,620 adjustably position the nasion pointer 604, the edentulous fork 608, and the centric relation recorder 610 respectively. The central bar 602 is normal to the ground in a direction indicated by axis-Y. The nasion pointer 604 is adjustably positionable through a first clamping assembly 614 to the central bar; the semi-circular frame 606 is adjustably positionable by the spring action of the semi-circular frame and it is attached to the central bar through the second clamping assembly 616. The edentulous fork 608 is adjustably positionable through a third clamping assembly 618, and the centric relation recorder 610 is adjustably positionable through a fourth clamping assembly 620. The first clamping assembly 614 clamps the nasion pointer 604 to the central bar 602, the second clamping assembly 616 clamps the semi-circular frame 606 to the central bar 602, the third clamping assembly 618 clamps the edentulous fork 608 and the fourth clamping assembly 620 clamps the centric relation recorder 610. The nasion pointer 604, the edentulous fork 608 and the centric relation recorder 610 are clamped such that the nasion pointer 604, the edentulous fork 608 and the centric relation recorder 610 are positioned along a predefined axis and are perpendicular to the axis-Y of the central bar.

The semi-circular frame 606 is attached such that the central bar 602 is anterior to the semi-circular frame 606 and the semi-circular frame is positionable by the spring action of the semi-circular frame. The semi-circular frame 606 includes two extreme ends, a left end 606A and a right end 606B. The orbital pointer 612 is positioned at a predefined position on the semi-circular frame 606 in close proximity of the right end 606B. The nasion pointer 604, the edentulous fork 608, the centric relation recorder 610 are attached such that they are adjustably positionable along a predefined Z axis through the clamping assemblies 614,618,620 respectively and are perpendicular to the Y axis of the central bar 602 facing towards the two extreme ends 606A and 606B of the semi-circular frame 606. It is to be noted that the device 600 has two combinations of reference points, wherein the first combination includes the two extreme ends 606A and 606B of the semi-circular frame 606 acting as the two posterior points of reference and the nasion pointer 604 acting as a first anterior point of reference depending upon the type of articulator used. Similarly, the second combination is the two extreme ends 606A and 606B of the semi-circular frame 606 acting as the two posterior points of reference and the orbital pointer 612 acting as a second anterior point of reference depending upon the type of articulator used. The device 600 of the present invention includes a pair of recorder, wherein the fourth clamping assembly 620 having the centric relation recorder 610 acts as the first recorder for recording the centric relation and the semi-circular frame 606 along with the two combinations of reference points acts as a second recorder for recording of orientation jaw relation of the edentulous subject.

Now referring to FIG. 6B, the third clamping assembly 618 of the device 600 for edentulous subjects is described. The third clamping assembly 618 includes plurality of screws, a lock 622 and a connector 624 for adjustably clamping the edentulous fork 608 to the central bar 602. The third clamping assembly 618 includes the lock 622, the connector 624, a first screw (Not shown), a second screw 626 for horizontal adjustment, a third screw 628 for forward and backward adjustment, and the edentulous fork 608. The edentulous fork 608 includes two ends, a first curved end having a C-clip 630 and a second straight end 632. The first curved end of the fork 608 fixedly attaches the C-clip 630 at a predefined position and the second straight end 632 of the fork 608 is receivable in the lock 622. The C-clip 630 is coupled to the curved end of the fork 608 by a cap 634 such that the cap 634 clamps the C-clip 630 and connects the C-clip 630 to the fork 608 and the respective screws 626 and 628 adjustably tighten the edentulous fork 608 according to a predefined requirement.

A one end of the connector 624 is horizontally receivable in the lock 622 at a predefined position and a other end of the connector 624 is receivable in a first lock (Not shown). The first lock receives the central bar 602 and that is lockable by first screw such that the connector 624 is perpendicular to the central bar 602 and is adjustable in horizontal direction. The lock (Not shown) is fixed to the central bar 602 with the respective screw (Not shown). The edentulous fork 608 is clamped such that the edentulous fork 608 is perpendicular to the Y-axis of the central bar 602. The edentulous fork 608 is adjustable in the horizontal direction along Z-2 axis by adjusting screw 626 and the forward and backward direction at a predefined position by adjusting the respective screw 628 to achieve a required length. The required length of the edentulous fork 608 is achieved by forward and backward movement of the second straight end 632 by loosening of the screw 628 and the edentulous fork 608 is locked at a predefined position as required by tightening of the respective screws.

The C-clip 630 of the edentulous fork 608 facilitates the fastening to maxillary and mandibular wax rims that are well known in the art. The edentulous fork 608 for the edentulous subjects is designed in such a way that it gets inserted in maxillary and mandibular wax rims anteriorly in the midline and can be sealed together.

In operation, referring to FIGS. 1 to 5, in a first step adjusting the adjustable fork 108 by loosening the screw 418 such that the two arms 416 of the adjustable fork do not come in between the subject's maxillary and mandibular teeth. Once the adjustment is done, wrapping a double layer of modelling wax or any other suitable recording material onto the adjustable fork 108 supporting the recording material from sides, followed by keeping it aside. In a next step, orienting the semi-circular frame 106 along the anterior side of the subject's face such that the pair of ear plugs 304 are inserted into the subject's respective ear and approximating the orbital pointer 112 accordingly in a predefined position at the level of infraorbital notch and the semi-circular frame 106 is parallel to the inter-pupillary line. For the articulators which need to be adjusted by using nasion as the third point of reference, a nasion pointer 104 is also provided.

It is to be noted that a subject's anterior occlusal jig is to be made by either acrylic resin or any other suitable material so that the subject's maxillary and mandibular teeth do not contact each other during any movement of the mandible i.e forward, backward and lateral etc. Further step includes fixing the centric relation recorder 110 over the subjects chin by adjusting the calibrated rod 508 as much as possible to a required length to ensure that the reading on the calibrated slider 510 is zero. This is followed by tightening of the screw 507 to fix the rod 508 and rotating 506 until a firm resistance is felt by the operator. Further step includes noting of the readings on both the calibrated rod 508 as well as the calibrated slider 510. This procedure is to be repeated preferably three times by keeping the occlusal jig in place to obtain a mean reading. A simultaneous step includes preparing the arms 416 of the adjustable fork 108 with double layer wax and softening of the wax or any other preferred material. Next step includes placing the centric relation recorder 110 again to previously noted reading without the occlusal jig by instructing the subject not to close his teeth. Once the predetermined reading is achieved, asking the subject to open his jaws so that operator can insert the adjustable fork 108 and instruct the subject to close in one go.

Ensuring that the semi-circular frame 106 is parallel to inter-pupillary line and it is firmly secured in the ears and then tighten the screw 410,412 in order to fix the adjustable fork 108. It is to be noted that if the articulator is designed to be adjusted with nasion reference point as third point of reference, there is no need to adjust orbital pointer 112, however the nasion pointer is fixed over the nose bridge and the respective screws are tightened. If, the articulator is designed to be adjusted with infra-orbital notch as a third reference point then nasion pointer need not be used. At this point, ensuring that all the respective screws are tightened and the orbital pointer 112 corresponds to the infra orbital notch, alternatively nasion pointer, if that is to be used as the third point of reference.

In a next step, loosening of all the respective screws of the centric relation recorder 110 and separating the clamping assembly from the central rod 102 by loosening screw 505. This is followed by loosening the nasion pointer 104 and/or the orbital pointer 112 and removing the semi-circular frame 106 that is around the anterior of the subject's face such that the ear plugs 304 are removed from the subject's ears along with the adjustable fork 108 having recorded indentations on to the recording wax material or any other suitable material which can get perforated wherever teeth come in contact.

Further step involves transferring of the obtained recorded indentations of the wax material to the semi adjustable articulator. For direct facebow transfer the semi-circular frame 106 is placed over the articulator along with adjustable fork 108 with recorded indentations in a conventional way. Maxillary and mandibular cast are correctly secured into the recorded indentations obtained from the subject. The third point of reference either nasion or infra-orbital indicator is used for orientation on the articulator. For indirect transfer, the semi-circular frame 106 is separated from the central rod 102 along with the assembly 114 and the recorded indentations are transferred to the semi adjustable articulator using a transfer jig of the articulator. Now the central rod 102 along with the assembly of adjustable fork 108 and screws 118 are fixed to the transfer jig of the semi adjustable articulator. Both, the maxillary and mandibular casts are further correctly oriented into the indentations obtained from subject. The mandibular cast is supported with modelling clay or carding wax. The maxillary cast is mounted with dental plaster. The articulator is reversed and mandibular cast is mounted. It is to be noted that the records obtained by using the device 100 can also be transferred to non-adjustable articulators known in the art.

In another embodiment, a method of using the device 600 of the present in edentulous subjects is disclosed. Adjusting of the vertical relation is required before using this device 600. There should not be gap between the maxillary and mandibular wax rims at occlusal vertical dimension. In a first step, orienting the semi-circular frame 606 along the anterior side of the subject's face such that the extreme ends 606A and 606B of the semi-circular frame 606 are inserted into the subject's respective ear.

In a next step, asking the subject to relax his/her mandible completely and fix a arcuate grip of the centric relation recorder 610 exactly over the centre of the chin such that the chin of the subject is in a relaxed position on the second straight end of the centric relation recorder 610. Fixing of the arcuate grip of the centric relation recorder 610 over the centre of the subject's chin and adjusting the required length of the second straight end of the centric relation recorder 610 by tightening the respective screw such that a strong resistance is felt by the operator. The centric relation recorder 610 is adjusted in forward and backward motion and is fastened using the screw 507. At the point of resistance, recording of the respective readings on the calibrated slider and rod of the centric relation recorder 610 is done. In order to obtain a mean reading, repeating the aforesaid disclosed step for at least three times and recording the readings.

After confirming that the readings are repeatedly same, asking the subject to maintain the mandible in same position, followed by inserting the edentulous fork 608. Designing of the edentulous fork 608 for edentulous subjects is done in such a way that C-clip 630 gets inserted in maxillary and mandibular wax rims anteriorly in the midline and can seal it together. In case of edentulous centric jaw relation recording device 600, the subject is not required to open his/her jaw, however only requires the insertion of the edentulous fork 608 to seal both the rims together in the anterior region in the midline. In order to seal both the rims perfectly, normal stapler pins are inserted additionally on either side buccally, such that half of the pin gets inserted in maxillary wax rim and half gets inserted into mandibular wax rim. The tips of the stapler pins can be inserted easily by heating it slightly over the flame before inserting. Ensure that the semi-circular frame 606 is parallel to inter-pupillary line and it is firmly secured in the ears and then tighten the respective screws in order to fix the edentulous fork. If the articulator is designed to be adjusted with nasion reference point as a third point of reference, there is no need to adjust orbital pointer, the nasion pointer is fixed over the nose bridge and the respective screws are tightened. If the articulator is designed to be adjusted with infra-orbital reference point then orbital pointer should correspond with the infra orbital notch and tighten its screws. At this point, ensuring that all the respective screws are tightened.

In a further next step, loosening of all the respective screws of the centric relation recorder 610 and separating the clamping assembly from the central rod by loosening screw located behind the bush 620. Then loosening the nasion pointer 604 and the orbital pointer 612 and removing the semi-circular frame 606 that is around the anterior of the subject's face such that the ear plugs 606A and 606B are removed from the subject's ears along with the edentulous fork 608 with its sealed maxillary and mandibular wax rims Next step involves transferring of the obtained recorded seal wax rims to the semi adjustable articulator. For direct facebow transfer, taking the semi-circular frame with maxillary and mandibular rims attached to the edentulous fork 608 and then maxillary and mandibular casts are placed into the respective rims correctly, then using third point of reference orient the semi-circular frame correctly on the articulator, mandibular cast to be supported by modelling clay and mount it according to a preferred method known in the art. For indirect facebow transfer, separating the semi-circular frame 606 from the central rod 602 along with the assembly 614. The central rod 602 along with the assembly of edentulous fork and screws 618 are fixed to the transfer jig of the semi adjustable articulator. Both, the maxillary and mandibular casts are further correctly oriented into the sealed maxillary and mandibular record bases. The mandibular cast is supported with modelling clay or carding wax. The maxillary cast is mounted with dental plaster. Then the articulator is reversed and mandibular cast is mounted.

It is to be noted that the centric relation records obtained by using the device 600 can also be transferred to non-adjustable articulators known in the art in case of edentulous subjects. In case of transfer of the records on semi-adjustable articulator, condylar guidance can be adjusted by making an interocclusal protrusive record at 6 mm forward position of the mandible from the readings recorded at centric relation position, wherein the mandibular wax rim is reduced by 2-3 mm in height, except in second molar region on either side and in the central incisors region for maintaining the vertical dimension. Inverted 'V' shaped notches are prepared on the maxillary wax rim in premolar and first molar region on either side. To obtain a protrusive reading 6 mm is subtracted from the said centric relation reading where a firm resistance was felt by the operator. The centric recorder assembly is fixed at said predefined protrusive reading and the recording material such as plaster of paris or any other suitable material is placed between the wax rims and the condylar guidance is adjusted according to said protrusive record. Further the lateral condylar guidance can be adjusted by using Hanau's formula $L=H/8+12$ which is known in the art.

In a preferred embodiment, device 100 and 600 for recording centric jaw relation and orientation jaw relation simultaneously of the present invention can also be used to perform orientation jaw relation or face-bow transfer such that, the recording of the centric jaw relation and orientation jaw relation is achieved in the single step, thereby avoiding multiple sittings or appointments. The device 100 and 600 for recording centric jaw relation and orientation jaw relation of the present invention helps in recording of the centric jaw relation accurately, and that has improved ergonomics and a user friendly design. The devices in the prior art fail to provide accurate centric jaw relation recording and that there is no simple device as that like the present invention which can record the complicated centric jaw relation. The device 100 and 600 advantageously include two combinations of reference points, namely first combination with nasion pointer and second with orbital pointer, which makes the device of the present invention novel. There is no device in art with two combinations of reference points and one can use any of the predefined combination of reference point depending upon the type of articulators used and can record centric relation. The device 100 and 600 of the present invention is applicable for any conventional semi-adjustable or non-adjustable articulators. The third point of reference may not be required in case of non-adjustable articulators. Further, in case of edentulous subject, the condylar guidance can be adjusted by making an interocclusal protrusive record obtained at 6 mm forward position of the mandible from centric relation reading. The present invention eliminates the drawbacks of the methods and devices disclosed in the prior art and provide a highly efficient and simple device with enhanced ease and comfort in operation, thereby reducing chances of injury to subject and provides improved efficiency in recording centric jaw relation and in achieving efficient face bow transfer. The device 100 and 600 of the present invention also reduces the number of appointments and thereby saves lot of time.

The purpose of the device 100 and 600 of the present invention is not only to simplify recording of centric jaw relation as per the description given in the glossary of prosthodontics (GPT)-8 but to make it a simple mechanical procedure where any dental surgeon can record a perfect centric jaw relation irrespective of whether the subject is dentulous or edentulous. The device 100 and 600 of the present invention is the first mechanical device which guides the condylar head in its centric jaw relation position as described in its definition. Present invention is designed to record the orientation jaw relation also and further it can be transferred to the articulator in the same sitting, thereby minimising multiple visits otherwise required. The device 100 of the present invention for recording centric jaw relation and orientation jaw relation simultaneously of dentulous subjects and device 600 for recording centric jaw relation and orientation jaw relation simultaneously of edentulous subjects is the unique device based on the latest definition of centric jaw relation as per GPT-8. The device 100 for recording centric jaw relation for dentulous subjects and device 600 for edentulous subjects of the present invention advantageously helps in an accurate and precise recording of the centric jaw relation mechanically.

The device 100 for recording centric jaw relation and orientation jaw relation simultaneously for dentulous subjects and device 600 of the present invention is designed in such a way that gives maximum comfort to the subjects. The device 100 for dentulous subjects and device 600 for edentulous subjects of the present invention guide the mandible in such a way that the head of the condyle in the glenoid fossa, along with its respective complexes, will attain most anterior and superior position on either side which is the centric jaw relation position. The device 100 for dentulous subjects and device 600 for edentulous subjects of the present invention is the only face bow compatible device with any existing articulators using different third points of references i.e. nasion and infraorbital notch. The device 100 for dentulous subjects and device 600 for edentulous subjects of the present invention provides an unique semi-circular frame that gives a better spring action that helps in improved stabilization of the semi-circular frame over the subject's face.

The device 100 for recording centric jaw relation for dentulous subjects of the present invention provides an adjustable fork for dentulous subjects' that is designed to record maxillary and mandibular occlusal record without any interference of the teeth, thereby customizing the bite adjustable fork according to the width of the subject's arch. The device 100 for dentulous subjects and device 600 for edentulous subjects of the present invention is the only device which records centric jaw relation as per the new definition of CR (GPT-8).

A person skilled in the art will appreciate that the device of the present invention if used according to the process disclosed above is very easy to use and is not cumbersome relative to the devices using graphical methods of the prior art. It will be further appreciated that the device of the present invention has got high adaptability among the learners because of the novel structure and standardized operational use as disclosed in the present invention.

The embodiments of the invention shown and discussed herein are merely illustrative of modes of application of the present invention. Reference to details in this discussion is not intended to limit the scope of the claims to these details, or to the figures used to illustrate the invention.

The invention claimed is:

1. A device for recording centric jaw relation and orientation jaw relation simultaneously of a dentulous subject in a single step comprising:
   a central bar;
   a first recorder comprising a semi-circular frame adjustably positionable on the central bar through a first clamping assembly, the semi-circular frame having a first end and a second end defining a pair of posterior reference points relative to the first clamping assembly of the semi-circular frame secured to the central bar;
   a centric relation recorder, comprising a calibrated rod, a calibrated slider and an arcuate grip, the calibrated rod having a predefined first main scale and the calibrated slider having a predefined second scale for recording a centric jaw relation of the dentulous subject through the arcuate grip according to the first main scale and the second scale of the calibrated rod and the calibrated slider, respectively, the calibrated slider being freely movable within the calibrated rod along a predefined axis thereof;
   a dentulous adjustable fork having a curved first end and a straight second end, the curved first end having a pair of arms attached at a predefined position, the arms facilitating fastening of a desired recording material to the dentulous adjustable fork and the second straight end adjustably positionable to the central bar through a second clamping assembly, in which a distance between the pair of arms is adjustable;
   a nasion pointer adjustably positionable vertically on the central bar through a third clamping assembly and adjustably positionable horizontally along a predefined axis through a fourth clamping assembly, the nasion pointer defining a first anterior point of reference; and
   an orbital pointer adjustably positionable on the semi-circular frame proximate the second end of the semi-circular frame, the orbital pointer defining a second anterior point of reference.

2. The device as claimed in claim 1, wherein the centric relation recorder, the nasion pointer and the adjustable fork are perpendicular to the central bar.

3. The device as claimed in claim 1, wherein the centric relation recorder, the nasion pointer and the adjustable fork are adjustably positioned at a predefined position on the central bar.

4. The device as claimed in claim 1, wherein the orbital pointer positions at a predefined location on the semi-circular frame such that the semi-circular frame is parallel to an inter-pupillary line.

* * * * *